United States Patent [19]

Hanack et al.

[11] 4,305,885
[45] Dec. 15, 1981

[54] PREPARATION OF CYCLOPROPANE-CARBOXYLIC ACID DERIVATIVES AND INTERMEDIATES THEREFOR

[75] Inventors: Michael Hanack; Theodor Stoll, both of Tübingen, Fed. Rep. of Germany

[73] Assignee: Bayer Aktiengesellschaft, Leverkusen, Fed. Rep. of Germany

[21] Appl. No.: 163,761

[22] Filed: Jun. 27, 1980

[30] Foreign Application Priority Data

Jul. 2, 1979 [DE] Fed. Rep. of Germany ....... 2926671

[51] Int. Cl.³ .................. C07C 121/46; C07C 121/48; C07C 69/747; C07C 69/753
[52] U.S. Cl. ............................. 260/464; 260/465 R; 560/8; 560/118; 560/124; 568/34; 568/35
[58] Field of Search ............... 260/464, 465 R; 560/8, 560/118, 124; 568/34, 35

[56] References Cited

U.S. PATENT DOCUMENTS

| | | | |
|---|---|---|---|
| 3,281,472 | 10/1966 | Heine | 568/35 |
| 3,445,499 | 5/1969 | Martel et al. | 260/464 |
| 3,578,717 | 5/1971 | Mitsch et al. | 568/35 |
| 3,853,952 | 12/1974 | Kishida et al. | 560/124 X |

FOREIGN PATENT DOCUMENTS

| | | |
|---|---|---|
| 1289046 | 2/1969 | Fed. Rep. of Germany . |
| 1668603 | 1/1974 | Fed. Rep. of Germany . |
| 2243371 | 3/1974 | Fed. Rep. of Germany . |
| 2500265 | 7/1976 | Fed. Rep. of Germany . |
| 2650534 | 5/1978 | Fed. Rep. of Germany . |

Primary Examiner—Dolph H. Torrence

Attorney, Agent, or Firm—Sprung, Felfe, Horn, Lynch & Kramer

[57] ABSTRACT

A perfluoroalkane-sulphinic acid of the formula $R_F$—$SO_2H$ is reacted with a diene at $-20°$ to $+20°$ C. to form the new intermediate $$\begin{array}{c} R^4 \quad\quad R^6 \;\; R^8 \\ \phantom{R^4}\diagdown \phantom{xx} | \;\;\; | \\ \phantom{xxx} C-C-CH-SO_2-R_F \\ \phantom{xx}\diagup \phantom{xx} | \;\;\; | \\ R^3 \quad\quad R^5 \;\; R^7 \end{array}$$

in which $R^3$–$R^8$ are hydrogen or various organic radicals or double bonds, and that is reacted with a $\beta,\beta$-dimethyl-acrylic acid derivative of the formula $$\begin{array}{c} CH_3\diagdown \\ \phantom{xx} C=CH-Z \\ CH_3\diagup \end{array}$$

in the presence of a base at a temperature between about $-20°$ and $+30°$ C. to produce a cyclopropane carboxylic acid derivative of the formula $$\begin{array}{c} R^1 \\ R^2 \diagdown\!\!\!\diagup Z \\ \diagup\;\;\diagdown \\ CH_3 \quad CH_3 \end{array}$$

in which Z is alkoxycarbonyl or cyano and $R^1$ and $R^2$ are hydrogen or various organic radicals. The products are known intermediates for insecticides.

11 Claims, No Drawings

PREPARATION OF CYCLOPROPANE-CARBOXYLIC ACID DERIVATIVES AND INTERMEDIATES THEREFOR

The invention relates to an unobvious process for the preparation of certain cyclopropane-carboxylic acid derivatives, and to perfluoroalkyl sulphones as new intermediate products for this process and to a process for their preparation.

It is already known that 2,2-dimethyl-3-(2-methyl-1-propenyl)-cyclopropane-1-carboxylic acid derivatives are obtained when aryl 3-methyl-2-butenyl sulphones are reacted with β,β-dimethyl-acrylic acid derivatives in the presence of bases (see DE-AS (German Published Specification) No. 1,289,046).

Very strong bases and anhydrous solvents are required to carry out this process. The yields are unsatisfactory, especially in the case of the preparation of the aryl 3-methyl-2-butenyl sulphones required as starting compounds.

The present invention now provides:

(1) a process for the preparation of a cyclopropane-1-carboxylic acid derivative of the general formula

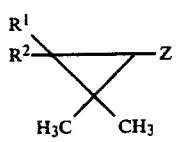

in which
 Z represents alkoxycarbonyl or cyano,
 $R^1$ represents hydrogen or alkenyl and
 $R^2$ represents hydrogen, or
 $R^1$ and $R^2$ together represent cycloalkyl or cycloalkenyl, onto which a benzene ring can optionally be fused, characterised in that a perfluoroalkyl sulphone of the general formula

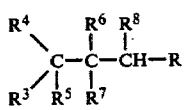

in which
 R represents the radical $-SO_2-R_F$,
 $R^3$ represents hydrogen or alkyl,
 $R^4$ represents alkyl or, together with $R^8$, forms an alkenediyl bridge, the double bond of which is optionally fused onto a benzene ring,
 $R^5$ and $R^6$ either represent hydrogen or together form a double bond,
 $R^7$ represents hydrogen or alkyl,
 $R^8$ represents hydrogen or alkyl and
 $R_F$ represents perfluoroalkyl, with the proviso that either $R^5$ and $R^6$ form a double bond or $R^8$ and $R^4$ form an alkenediyl bridge, the double bond of which is optionally fused onto a benzene ring,
is reacted with a β,β-dimethyl-acrylic acid derivative of the general formula

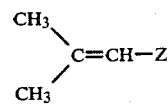

in which Z has the meaning indicated above, in the presence of a base and if appropriate in the presence of a diluent, at a temperature between $-20°$ and $+30°$ C.;

(2), as new compounds, the perfluoroalkyl sulphones of the general formula

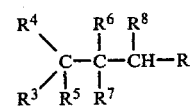

in which R and $R^3-R^8$ have the meanings indicated above; and (3) a process for the preparation of a perfluoroalkyl sulphone of the formula (II) above, characterized in that a perfluoroalkane-sulphinic acid of the general formula $$R_F-SO_2H \qquad (IV),$$

in which $R_F$ represents perfluoroalkyl, is reacted with a diene of the general formula

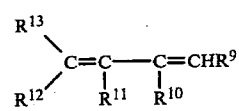

in which
 $R^9-R^{13}$ represent hydrogen or alkyl, it being possible for $R^9$, together with $R^{13}$, to represent an alkylene bridge, onto which a cycloalkene ring is optionally fused,
if appropriate in the presence of a diluent, at a temperature between $-20°$ and $+20°$ C.

It is surprising that cyclopropane-1-carboxylic acid derivatives of the formula (I) can be prepared in good yields and in high purity by using perfluoroalkyl sulphones of the formula (II), since in the known synthesis method, in which corresponding aryl sulphones are employed, only moderate yields which are difficult to reproduce are to be achieved.

It is furthermore surprising that the new perfluoroalkyl sulphones of the formula (II) can be synthesized in high yields by an addition reaction of perfluoroalkane-sulphinic acids onto dienes which is simple to carry out. The combination of the two new processes presents an industrially advantageous possibility of preparing derivatives of cyclopropanecarboxylic acid which are intermediate products for pyrethroids.

If, for example, perfluoromethanesulphinic acid and isoprene are used as starting substances in process (3) and β,β-dimethyl-acrylonitrile is used as the further reactant in the reaction in process (1) to be carried out with the (3-methyl-2-butenyl) trifluoromethyl sulphone thereby formed, the courses of the reactions can be outlined by the following equation:

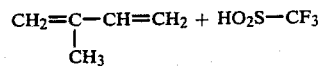

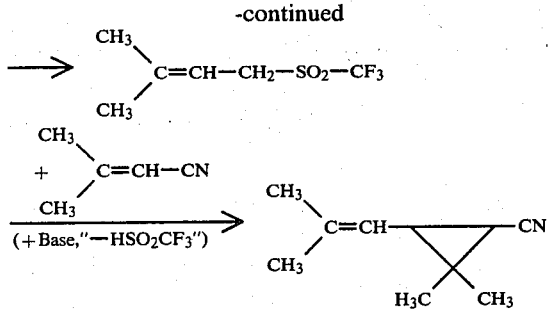

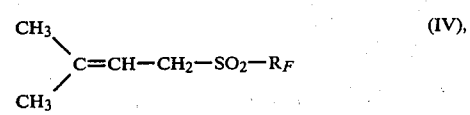

The new process described under (1) ("process (1)") is preferably carried out using a diluent. Possible diluents are virtually any of the organic solvents. Particularly suitable solvents are alcohols, for example methanol, ethanol and n- and iso-propanol, and, especially, aprotic polar solvents. These include, for example, ethers, for example diethyl ether, glycol dimethyl ether, tetrahydrofuran and dioxane; nitriles, for example acetonitrile and propionitrile; carboxylic acid amides, for example dimethylformamide and dimethylacetamide; sulphoxides and sulphones, for example dimethylsulphoxide and tetramethylenesulphone; and phosphoric acid amides, for example hexamethylphosphoric acid triamide. Tetrahydrofuran is the particularly preferred solvent.

Any of the bases customary in organochemical synthesis can be used in process (1). These bases include, in particular, alkali metal hydroxides and alkaline earth metal hydroxides, for example sodium hydroxide, potassium hydroxide or calcium hydroxide, alkali metal alcoholates, for example sodium methylate, potassium methylate, sodium ethylate, potassium ethylate, sodium tert.-butylate and potassium tert.-butylate, and furthermore aliphatic, aromatic and heterocyclic amines, for example triethylamine, ethyl diisopropylamine, N,N-dimethyl-benzylamine, N,N-dimethyl-aniline, pyridine, N-methyl-piperidine and diazabicyclononane. Alcoholates are particularly preferred as the bases in process (1).

The reaction temperature in process (1) is kept between about −20° and +30° C,. preferably between about −15° and +25° C. The reaction is in general carried out under normal pressure.

In general, between 1 and 5 mols, preferably between 1.5 and 4 mols, of $\beta,\beta$-dimethyl-acrylic acid derivative of the formula (III) are employed per mol of perfluoroalkyl sulphone of the formula (II).

In a preferred embodiment of process (1), most of the base to be employed is initially introduced in one of the above-mentioned diluents under an inert gas atmosphere, for example under nitrogen, and is cooled to about 0° to −15° C. The acrylic acid derivative of the formula (III) and the sulphone of the formula (II) are then slowly added dropwise, one after the other. The complete reaction mixture is stirred at 0° to −15° C., then about −5° to +5° C. and finally about +15° to +25° C., in each case for several hours. The mixture is then cooled again to the initial temperature, about 1/10 of the amount of base initially employed is added and the mixture is stirred at the various temperatures, as indicated above.

If appropriate, this operation is repeated several times. Working up can be carried out by customary methods, for example by pouring the reaction mixture into water and extracting it with a water-immiscible solvent, for example diethyl ether, drying the non-aqueous phase and, after filtration, distilling off the solvent. The product which remains after this procedure can be purified by vacuum distillation. It is characterized by its IR spectrum and its NMR spectrum.

Formula (II) provides a definition of the new perfluoroalkyl sulphones which are to be used as starting substances for process (1) according to the invention. Perfluoroalkyl sulphones of the general formula $$\begin{matrix} CH_3 \\ \diagdown \\ \diagup \\ CH_3 \end{matrix} C=CH-CH_2-SO_2-R_F \quad (IV),$$

in which
$R_F$ represents perfluoroalkyl with 1–8 C atoms, are preferred.

Examples of the compounds of the formula (II) which may be mentioned are perfluoromethyl 3-methyl-2-butenyl sulphone, perfluorobutyl 3-methyl-2-butenyl sulphone.

The new perfluoroalkyl sulphones of the formula (II) are obtained by the process described above under (3) ("process (3)"), by reacting perfluoroalkanesulphinic acids with dienes.

Formula (IV) provides a definition of the perfluoroalkanesulphinic acids to be employed as starting substances in this process. Preferably, in this formula,
$R_F$ represents perfluoroalkyl with 1 to 8 carbon atoms.

Examples of the starting substances of the formula (IV) which may be mentioned are perfluoromethanesulphinic acid, perfluorobutanesulphinic acid and perfluorooctanesulphinic acid.

Perfluoroalkanesulphinic acids are known compounds (see Liebigs Ann. Chem. 1973, 33).

Formula (V) provides a definition of the dienes also to be used as starting substances. Preferably, in this formula.
$R^9$ represents hydrogen or methyl or, together with $R^{13}$, methylene or ethylene,
$R^{10}$ and $R^{11}$ represent hydrogen or methyl and
$R^{12}$ and $R^{13}$ represent hydrogen or methyl, it being possible for $R^{12}$ and $R^{11}$, together with the C atoms adjacent to them, to form a benzene ring.

Examples of the starting compounds of the formula (V) which may be mentioned are: 1,3-butadiene, 1,3-pentadiene, 2,4-hexadiene, 2,3-dimethyl-1,3-butadiene, 2-methyl-1,3-butadiene, cyclopentadiene, indene and cyclohexadiene.

Process (3) can be carried out without using a solvent. However, it is also possible to use the polar solvents indicated above for process (1), a well as non-polar or slightly polar solvents, such as aliphatic or aromatic, optionally halogenated, hydrocarbons, for example pentane, hexane, heptane, toluene, chlorobenzene, methylene chloride, chloroform or 1,2-dichloroethane.

The reaction temperature is kept from about −20° to +20° C., preferably about −10° to +10° C., in process (3). In general, the process is carried out under normal pressure.

About 1 to 5 mols, preferably about 1.5 to 3 mols, of diene of the formula (V) are employed per mol of perfluoroalkanesulphinic acid of the formula (IV) in process (3).

In a preferred embodiment of process (3), the perfluoroalkanesulphinic acid is initially introduced into the reaction vessel and the diene, e.g. isoprene, is added dropwise, in excess. Working up is effected in the customary manner: the reaction mixture is poured into ice-water, neutralized and extracted with a water-immiscible solvent, such as, for example, diethyl ether. After drying and filtering the non-aqueous phase, the solvent is distilled off. The product obtained as the residue can be purified by vacuum distillation. It is characterized by its IR spectrum and NMR spectrum.

Formula (III) provides a definition of the β,β-dimethyl-acrylic acid derivatives to be employed as starting substances in process (1), in addition to the new sulphones of the formula (II). Preferably, in formula (III), Z represents alkoxycarbonyl with 1 to 4 carbon atoms in the alkoxy radical, or cyano.

Examples of the starting substances of the formula (III) which may be mentioned are β,β-dimethyl-acrylic acid methyl ester, ethyl ester, n-propyl ester, iso-propyl ester, n-butyl ester, iso-butyl ester, sec.-butyl ester and tert.-butyl ester and β,β-dimethyl acrylonitrile. The methyl ester and the ethyl ester are particularly preferred.

β,β-Dimethyl-acrylic acid derivatives of the formula (III) are known (see DE-AS (German Published No.) 1,289,046).

The cyclopropane-1-carboxylic acid derivatives of the formula (I) to be prepared by the process according to the invention can be used as intermediate products for the preparation of insecticidally and acaricidally active pyrethroids (see DE-AS (German Published) No. 1,289,046 and DE-OS (German Published) No. 2,605,828).

EXAMPLE

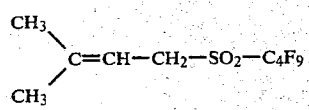
(a)

25 g (0.088 mol) of perfluorobutanesulphinic acid were initially introduced into a 100 ml three-necked flask and cooled to 0° C. Freshly distilled isoprene was then added dropwise, in excess, during which a dropping rate of 1 drop per minute had to be maintained. After the dropwise addition, the solution was immediately poured into ice-water neutralized with NaHCO$_3$ and extracted with ether. After drying with MgSO$_4$, the ether extract was filtered, the ether was stripped off from the filtrate in a rotary evaporator and the residue was distilled. Perfluorobutyl 3-methyl-2-butenyl sulphone of boiling point 41° C./0.1 mm Hg was obtained as a yellowish-tinged liquid in a yield of 60 to 70% of theory.

Characterization by the spectra:

$^1$H-NMR (CCl$_4$): δ=1.79 (S, 3H, methyl protons), 1.87 (s, 3H, methyl protons), 4.05 (d, 2H, methylene protons) and 5.27 (t, 1H vinyl proton) ppm.

IR (film): 3000 (olefinic C—H), 2930 (aliphatic C—H), 1660 (double bond), 1450 (—CH$_3$), 1370, 1145 (SO$_2$) and 1200–1250 (C$_4$F$_9$) cm$^{-1}$.

The following compounds could be prepared analogously:

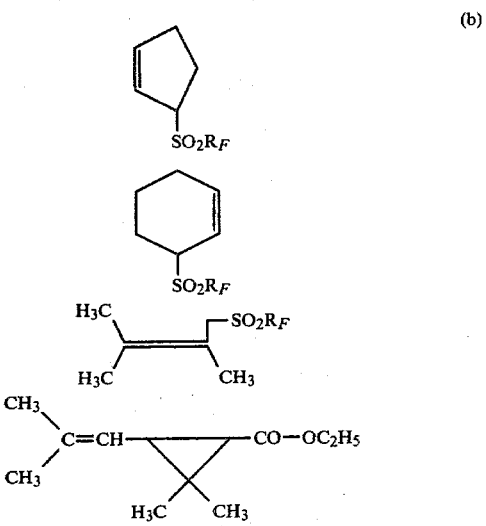
(b)

22 g of β,β-dimethyl-acrylic acid ethyl ester were added dropwise to a mixture of 10 g of potassium tert.-butylate and 100 ml of tetrahydrofuran, which had been cooled to −10° C. and gassed with nitrogen. A solution of 17 g of perfluorobutyl 3-methyl-2-butenyl sulphone in 20 ml of tetrahydrofuran was then very slowly added dropwise, while stirring vigorously. The reaction mixture was stirred for a further 12 hours at −10° C., for 12 hours again at 0° C. and for 24 hours at room temperature. It was then cooled again to −10° C. and a solution of 1 g of potassium tert.-butylate in 20 ml of tetrahydrofuran was added dropwise. The temperature was increased as described above. This operation was repeated twice more. The mixture was poured into water and an extraction was carried out with diethyl ether. The ether extract was dried over magnesium sulphate, filtered and concentrated. After distillation under reduced pressure, 2,2-dimethyl-3-(2-methyl-1-propenyl)-cyclopropane-1-carboxylic acid ethyl ester of boiling point 70° C./5 mm Hg was obtained as a colorless liquid in a yield of 60% of theory.

Characterization by the spectra:

$^1$H-NMR (CCl$_4$): δ=1.2 (m, 10H, methyl protons and cyclopropyl proton), 1.72 (s, 7H, methyl protons and cyclopropyl proton), 4.08 (q, 2H, methylene protons) and 4.87 (d, 1H, vinyl proton) ppm.

IR (film): 3010 (olefinic C—H), 1735 (ester-carbonyl), 1670 (double bond), 1455 (—CH$_3$) and 1390 (—CH$_3$) cm$^{-1}$.

It will be appreciated that the instant specification and examples are set forth by way of illustration and not limitation, and that various modifications and changes may be made without departing from the spirit and scope of the present invention.

We claim:

1. A process for the preparation of a cyclopropane-1-carboxylic acid derivative of the formula

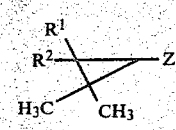

in which
Z represents alkoxycarbonyl or cyano, $R^1$ represents hydrogen or alkenyl and
$R^2$ represents hydrogen, or
$R^1$ and $R^2$ together represent cycloalkyl or cycloalkenyl, onto which a benzene ring can optionally be fused,
comprising reacting a perfluoroalkyl sulphone of the formula

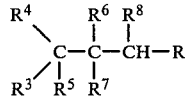

in which
  R represents the radical $-SO_2-R_F$,
  $R^3$ represents hydrogen or alkyl,
  $R^4$ represents alkyl or, together with $R^8$, forms and alkenediyl bridge, the double bond of which is optionally fused onto a benzene ring,
  $R^5$ and $R^6$ either represent hydrogen or together form a double bond,
  $R^7$ represents hydrogen or alkyl,
  $R^8$ represents hydrogen or alkyl and
  $R_F$ represents perfluoroalkyl, with the proviso that either $R^5$ and $R^6$ form a double bond or $R^8$ and $R^4$ form an alkenediyl bridge, the double bond of which is optionally fused onto a benzene ring, with a $\beta,\beta$-dimethyl-acrylic acid derivative of the formula

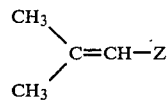

in the presence of a base at a temperature between about $-20°$ C. and $+30°$ C.

2. A process according to claim 1, wherein the perfluoroalkyl sulphone has the formula

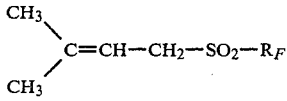

in which $R_F$ is perfluoroalkyl with 1-8 C atoms.

3. A process according to claim 1, in which
Z is alkoxycarbonyl with 1 to 4 C atoms in the alkoxy radical, or cyano.

4. A process according to claim 1, wherein the reaction is effected in the presence of a diluent comprising an alcohol or an aprotic polar solvent.

5. A process according to claim 1, wherein the reaction is effected in the presence of tetrahydrofuran as a diluent.

6. A process according to claim 1, wherein the base is an alkali metal hydroxide, an alkaline earth metal hydroxide, an alkali metal alcoholate or an aliphatic, aromatic or heterocyclic amine.

7. A process according to claim 1, wherein the reaction is effected between about $-15°$ and $+25°$ C.

8. A process according to claim 1, wherein between about 1 and 5 mols of the acrylic acid derivative are employed per mol of the sulphone.

9. A process according to claim 6, in which
Z is alkoxycarbonyl with 1 to 4 C atoms in the alkoxy radical, or cyano,
the perfluoroalkyl sulphone has the formula

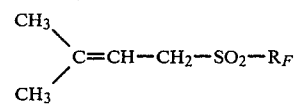

the reaction is effected between about $-15°$ to $+25°$ C. in the presence of tetrahydrofuran as a diluent, and between about 1.5 and 4 mols of the acrylic acid derivative are employed per mol of the sulphone.

10. A process according to claim 9, wherein the sulphone is produced by reacting a perfluoroalkane-sulphinic acid of the formula $R_F-SO_2H$ with a diene of the formula

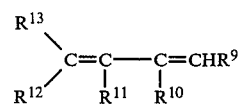

in which $R^9-R^{13}$ each independently is hydrogen or alkyl, it being possible for $R^9$, together with $R^{13}$, to represent an alkylene bridge, onto which a cycloalkene ring is optionally fused,
at a temperature between about $-20°$ and $+20°$ C.

11. A process for the preparation of a perfluoroalkyl sulphone of the formula

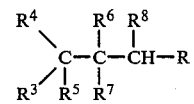

in which
  R represents the radical $-SO_2-R_F$,
  $R^3$ represents hydrogen or alkyl,
  $R^4$ represents alkyl or, together with $R^8$, forms an alkenediyl bridge, the double bond of which is optionally fused onto a benzene ring,
  $R^5$ and $R^6$ either represent hydrogen or together form a double bond,
  $R^7$ represents hydrogen or alkyl,
  $R^8$ represents hydrogen or alkyl and
  $R_F$ represents perfluoroalkyl,
comprising reacting a perfluoroalkane-sulphinic acid of the formula $R_F-SO_2H$
in which $R_F$ is perfluoroalkyl,
with a diene of the formula

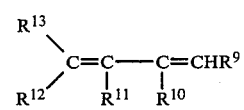

in which $R^9-R^{13}$ each independently is hydrogen or alkyl, it being possible for $R^9$, together with $R^{13}$, to represent an alkylene bridge, onto which a cycloalkene ring is optionally fused,
at a temperature between about $-20°$ and $+20°$ C.

* * * * *